(12) United States Patent
Suovaniemi

(10) Patent No.: US 10,092,534 B2
(45) Date of Patent: Oct. 9, 2018

(54) COMPOSITION FOR TREATING HEADACHES

(71) Applicant: BIOHIT OYJ, Helsinki (FI)

(72) Inventor: Osmo Suovaniemi, Helsinki (FI)

(73) Assignee: BIOHIT OYJ, Helsinki (FI)

( * ) Notice: Subject to any disclaimer, the term of this patent is extended or adjusted under 35 U.S.C. 154(b) by 285 days.

(21) Appl. No.: 14/397,563

(22) PCT Filed: May 28, 2013

(86) PCT No.: PCT/FI2013/050582
§ 371 (c)(1),
(2) Date: Oct. 28, 2014

(87) PCT Pub. No.: WO2013/178880
PCT Pub. Date: Dec. 5, 2013

(65) Prior Publication Data
US 2015/0132275 A1    May 14, 2015

(30) Foreign Application Priority Data
May 28, 2012 (FI) ...................... 20125570

(51) Int. Cl.
| | |
|---|---|
| A61K 31/195 | (2006.01) |
| A61K 31/198 | (2006.01) |
| A61K 9/00 | (2006.01) |
| A61K 9/68 | (2006.01) |
| A61K 9/20 | (2006.01) |
| A61K 38/06 | (2006.01) |
| A61K 38/44 | (2006.01) |

(52) U.S. Cl.
CPC ............ *A61K 31/198* (2013.01); *A61K 9/006* (2013.01); *A61K 9/0056* (2013.01); *A61K 9/0058* (2013.01); *A61K 9/2018* (2013.01); *A61K 9/2054* (2013.01); *A61K 38/063* (2013.01); *A61K 38/44* (2013.01); *C12Y 104/03022* (2013.01); *A61K 31/195* (2013.01)

(58) Field of Classification Search
CPC .................................................. A61K 31/195
USPC ........................................................ 514/562
See application file for complete search history.

(56) References Cited

U.S. PATENT DOCUMENTS

| 6,294,520 B1 | 9/2001 | Naito |
| 6,726,939 B1 | 4/2004 | Pak |
| 2008/0057110 A1 | 3/2008 | Skirpa |
| 2008/0075710 A1 | 3/2008 | Cornett et al. |
| 2011/0064711 A1 | 3/2011 | Eidenberger |

FOREIGN PATENT DOCUMENTS

| CN | 1486177 A | 3/2004 |
| EP | 2 374 448 A1 | 10/2011 |
| JP | 2004-512353 A | 4/2004 |
| JP | 2006-130488 A | 5/2006 |
| JP | 2007-522254 A | 8/2007 |
| JP | 2008-515859 A | 5/2008 |
| JP | 2009-522376 A | 6/2009 |
| JP | 2009-538832 A | 11/2009 |
| WO | 02/36098 A1 | 5/2002 |
| WO | 2005/077464 A1 | 8/2005 |
| WO | 2006/037848 A1 | 4/2006 |
| WO | 2006/103316 A1 | 10/2006 |
| WO | 2007/112138 A2 | 10/2007 |
| WO | 2007/135241 A2 | 11/2007 |
| WO | 2007/135242 A1 | 11/2007 |
| WO | 2009/034232 A1 | 3/2009 |
| WO | 2012/027603 A2 | 3/2012 |

OTHER PUBLICATIONS

Finnish Search Report for FI 20125570 dated Mar. 28, 2013.
International Search Report for PCT/FI2013/050582 dated Sep. 5, 2013.
Peatfield R.: "Headache," 1986, Springer, pp. 44-45 (4 pages total).
Rainero, MD, PhD et al., "Cluster Headache is Associated With the *Alcohol Dehydrogenase 4 (ADH4)* Gene," Research Submission; Headache; American Headache Society (Jan. 2010) pp. 92-98.
López-Mesonero et al., "Smoking as a precipitating factor for migraine: a survey in medical students," J Headache Pain (2009) vol. 10; pp. 101-103.
Translation of Communication dated Jun. 27, 2017, from the Russian Patent Office in counterpart application No. 2014143120/15.
Patricia B.E. Woolsey "Cysteine, Sulfite, and Glutamate Toxicity: A Cause of ALS?" The Journal of Alternative and Complementary Medicine vol. 14, No. 9, 2008 (pp. 1159-1164).
Mala Srivastava "Dangers of Taking L-Cysteine" Livestrong.com, Dec. 5, 2015 (3 pages total).

*Primary Examiner* — Kevin E Weddington
(74) *Attorney, Agent, or Firm* — Sughrue Mion, PLLC (57) ABSTRACT

The present invention concerns a non-toxic solid pharmaceutical composition for oral administration, containing one or more cysteine compounds from the group of L-cysteine, D-cysteine and N-acetyl cysteine, combined with one or more additional active agents, at least one of which being selected from cystine, glutathione and methionine, the composition further containing one or more pharmaceutical additives. Further, the invention concerns a method for reducing the incidence of severe headaches, particularly migraine and/or cluster headaches.

33 Claims, 2 Drawing Sheets

COMPOSITION FOR TREATING HEADACHES

CROSS REFERENCE TO RELATED APPLICATIONS

This application is a National Stage of International Application No. PCT/FI2013/050582 filed May 28, 2013, claiming priority based on Finnish Patent Application No. 20125570 filed May 28, 2012, the contents of all of which are incorporated herein by reference in their entirety.

FIELD OF THE INVENTION

The present invention concerns a non-toxic oral pharmaceutical composition for reducing the incidence of, or preventing, or at least relieving, severe headaches, particularly migraines or cluster headaches. Further, the invention concerns a method for reducing the incidence of, or preventing such severe headaches.

DESCRIPTION OF RELATED ART

Cluster headache is a neurological disease that involves, as its most prominent feature, excruciating unilateral headaches of extreme intensity. "Cluster" refers to the tendency of these headaches to occur periodically, with active periods interrupted by spontaneous remissions. The cause of the disease is currently unknown. It affects approximately 0.1% of the population.

While migraines are diagnosed more often in women, cluster headaches are more prevalent in men. The male-to-female ratio in cluster headache is about 5:1. It primarily occurs between the ages of 20 to 50 years.

In Finland alone, over 15 000 people suffer from Cluster Headaches (about 0.3% of the population). The number of people suffering from migraine is even larger (10 to 20% of the population).

The duration of the common attack ranges from as short as 15 minutes to three hours or more. If untreated, the attack frequency is from 1 to 16 attacks in 48 hours. The headache may be accompanied by one or more of the following autonomic symptoms: ptosis (drooping eyelid), miosis (pupil constriction), conjunctival injection (redness of the conjunctiva), lacrimation (tearing), rhinorrhea (runny nose), and, less commonly, facial blushing, swelling, or sweating, all appearing on the same side of the head as the pain.

The onset of an attack is rapid, and most often without the preliminary signs that are characteristic of a migraine.

Cluster headaches are occasionally referred to as "alarm clock headaches" because of their ability to wake a person from sleep and because of the regularity of their timing: both the individual attacks and the clusters themselves can have a metronomic regularity; attacks striking at a precise time of day each morning or night is typical, even precisely at the same time a week later. The clusters tend to follow daylight saving time changes and happen more often in spring and fall equinox. This has prompted researchers to speculate an involvement of the brain's "biological clock" or circadian rhythm.

In episodic cluster headaches, the attacks occur once or more often daily, often at the same times each day, for a period of several weeks, or even months, followed by a headache-free period lasting weeks, months, or years. These episodes often occur during the same season, e.g. during the autumn or the spring.

However, approximately 10-15% of cluster headache sufferers are chronic, and they can experience multiple headaches every day for years. About 10% of episodic cluster headaches turn into the chronic type at some point in time.

Cluster headaches are sometimes classified as vascular headaches. The intense pain has been suggested to be linked with the dilation of blood vessels which creates pressure on the trigeminal nerve. While this process is seen as the immediate cause of the pain, the etiology is not fully understood.

The episodes are known to be triggered by factors, such as alcohol consumption, changes in sleeping habits, excess physical strain, outbursts of anger and pressure variations (e.g. during flights or mountain climbs). A link has also been implied between these episodes and smoking.

The last mentioned affliction is often found in people with a heavy addiction to cigarette smoking. There are also cases where second hand smoke has been shown to trigger cluster headaches.

Sensitivity to alcohol during a cluster bout also occurs. Patients who are sensitive to alcohol note that attacks are triggered within 5 to 45 minutes after the ingestion of modest amounts of alcohol, usually being less than a single cocktail or glass of wine. Alcohol triggers attacks in 70 to 80% of exposures.

Experimentally, attacks can be triggered in nearly all patients during a bout by the administration of nitroglycerin or histamine. Histamine most likely functions by triggering an inflammatory response.

It has also been shown that mast cells, the major repository of histamine in many tissues, are found in increased number in the skin of the painful temporal area in cluster headache patients. This effect is also found in migraine patients.

Cluster headaches are benign, but because of the extreme and debilitating pain associated with them, and potential risk of suicide, a severe attack is nevertheless treated as a medical emergency. Because of the relative rareness of the condition and ambiguity of the symptoms, some sufferers may not receive treatment in the emergency room and people may even be mistaken as exhibiting drug-seeking behavior.

There are other types of headache that are sometimes mistaken for cluster headaches, such as Chronic Paroxysmal Hemicrania (CPH) and ictal headache.

Medications to treat cluster headaches are classified as either abortive (e.g. cortisone, migraine medicines, ergotamine tartrate, naratriptan, frovatriptan or a local anesthetic to the occipital nerve) or prophylactics (preventatives, e.g. verapamil, lithium, sodium valproate, topiramate, baclofen, melatonin, methysergide, indomethacin or capsaicin). In addition, short-term transitional medications (such as steroids) may be used while prophylactic treatment is instituted and adjusted.

European guidelines suggest the use of the calcium channel blocker verapamil. Steroids, such as prednisolone/prednisone, are also used. Methysergide, lithium and the anticonvulsant topiramate are recommended as alternative treatments.

Over-the-counter pain medications (such as aspirin, paracetamol, and ibuprofen) typically have no effect on the pain from a cluster headache. The treatment is generally selected based on the individual's experience, after testing various medications. No reliable test results have been available.

However, the present inventors have surprisingly found that a pharmaceutical composition decreasing the amount of acetaldehyde carried to or formed in the body of a human subject will alleviate and prevent these severe headaches, particularly cluster headaches, which could provide a link between these headaches and said alcohol consumption as well as smoking.

The first metabolite of alcohol is acetaldehyde. The alcohol is evenly distributed in the liquid phase of the organs. Hence, after enjoying alcohol and as long as there is alcohol in the organs, the alcohol content in the blood, saliva, gastric juice and the contents of the intestine is the same. The acetaldehyde is formed from the alcohol, among others, through microbial action. Microbes, among others in the digestive tract, are capable of oxidizing alcohol to acetaldehyde. For example, even after a moderate dose of ethanol (0.5 g/kg), high acetaldehyde contents of a microbial origin (18-143 µM) have been found in human saliva. In other words, acetaldehyde builds up in the saliva as an intermediate product of the microbial metabolism (Homann et al, Carcinogenesis (1997) 18:1739-1743).

In the organism, acetaldehyde is thus formed from alcohol as a consequence of the hepatic metabolism and, locally, in the digestive tract via microbial alcohol dehydrogenase (Salaspuro et al, (1996) Ann Med 28:195-200). The saliva spreads from the mouth to the other areas of the digestive tract, whereby areas of influence of the acetaldehyde contained in the saliva include the mouth, the pharynx, the oesophagus and the stomach. Consequently, the effects of acetaldehyde may extend to the whole upper digestive tract area.

It has also been shown that acetaldehyde builds up in the large intestine, as its bacteria that represent the normal flora are capable of converting ethanol into acetaldehyde (Jokelainen et al, (1996) Gut 39:100-104). In the intestines, endogenous ethanol can also be found, i.e. ethanol that is formed in the intestines in oxygen-free conditions under the effect of microbes. Acetaldehyde is formed, when this ethanol comes into contact with oxygen near the mucous membrane, for example.

On the other hand, carcinogenic acetaldehyde can be produced also endogenously by the oral microbes from various foodstuffs with high sugar or carbohydrate content, which will cause an increased acetaldehyde-content also in the stomach, especially in subjects suffering from an achlorhydric stomach.

Our recent studies have shown that all sugar (saccharose, maltose, lactose)-containing foodstuffs including beverages, can contain significant amounts of acetaldehyde, 5 to 2000 µM and ethanol, 0.1 to 0.5 per mille, or the acetaldehyde can be formed in the foodstuff. Some sour milks, yoghurts and juices contain acetaldehyde and ethanol, as such (PCT/FI2006/000104 incorporated herein by reference).

During active smoking, the acetaldehyde in the saliva was also increased to a value of 261.4±45.5 µM from the basic level (Salaspuro et al. (2004) Int J Cancer, 2004 Sep. 10; 111(4):480-3).

The prior art discloses pharmaceutical compositions which contain compounds that bind acetaldehyde, their effect being based on the reaction of the effective substances with the acetaldehyde inside blood and/or cells, for example, U.S. Pat. No. 5,202,354, U.S. Pat. No. 4,496,548, U.S. Pat. No. 4,528,295, U.S. Pat. No. 5,922,346.

When such a composition is swallowed, the effective substances are instantly taken to the small intestine and from there into the blood circulation (Matsuoka, U.S. Pat. No. 5,202,354 and Moldowan et al, U.S. Pat. No. 4,496,548).

Suggestions have been made so as to use preparations containing amino acids and vitamins, which are sucked or chewed in the mouth, to reduce the liver-mediated effect of detrimental free-radical compounds, which are formed when using tobacco products or being exposed to the same. It is believed that, after being absorbed, amino acids affect various tissues (Hersch, U.S. Pat. No. 5,922,346, Hersch, International Patent Application WO 99/00106). However, in all these cases, the effect is merely systemic.

Publication WO 02/36098 (incorporated herein by reference) suggests the use of a compound containing a free sulphhydryl and/or amino group for a local and long-term binding of acetaldehyde from saliva, the stomach or the large intestine. The compound was mixed with a substance that enabled it to be released for at least 30 minutes in the conditions of the mouth, the stomach or the large intestine. In this case, the effect is limited to the gastrointestinal tract.

Publication WO 2006/037848 (incorporated herein by reference) suggests a composition comprising a compound containing one or more free sulphhydryl and/or amino group for removing or decreasing the aldehyde content of the saliva during smoking. Also this effect is only local.

However, none of the prior art suggests using cysteine or cystine or other similar compounds to relieve or prevent any types of headache. Further, no combination products have been developed.

Based on our recent studies, acetaldehyde plays a part in causing severe headaches, particularly cluster headaches and migraines. Since these conditions cannot yet be effectively prevented, and all existing prophylactic medicines have severe side effects, there is thus a need to find alternative and mild ways to at least relieve the symptoms or reduce the number of episodes in subjects suffering from these severe headaches.

SUMMARY OF THE INVENTION

It is an aim of the present invention to provide new compositions, which can be used to prevent or at least reduce the incidence of episodes of severe headaches, such as cluster headaches, migraine, ictal headache or chronic paroxysmal hemicrania.

It is also an aim of the present invention to provide new methods and uses for treating people diagnosed to suffer from cluster headaches or migraine.

Particularly, it is an aim of the invention to provide compositions, which can be used in the treatment or prevention of severe headaches, and which mask the taste of the active agents.

These and other objects, together with the advantages thereof over known products and methods, are achieved by the present invention, as hereinafter described and claimed.

Compositions containing one or more cysteines as active agents have been shown to bind acetaldehyde. These active agents have been found to also be capable of breaking down biofilms formed by some microbes, particularly in the stomach. Also at least a partial eradication of microbes can be accomplished using a composition containing a cysteine, although this effect might be a result of the destruction of the biofilms, whereby the stomach acids are able to attack the microbes.

All the above mentioned effects of compositions containing one or more cysteines have been shown to be successful also in subjects having achlorhydria, or a low-acid stomach, often linked to *H. pylori* infections. To estimate the magnitude of the problems caused by acetaldehyde in the gastrointestinal tract (GI tract), it would be recommendable to start any treatment with a diagnosis as to the possible *H. pylori* infection.

The composition of the present invention can be used to prevent cluster headaches (CHA), regular migraines or both, or even ictal headaches or chronic paroxysmal hemicrania.

Thus, the present invention concerns a non-toxic solid pharmaceutical composition for oral administration, containing one or more agent from the group of L-cysteine, D-cysteine and N-acetyl cysteine, combined with one or more agent selected from cystine, glutathione and methionine.

More specifically, the composition of the present invention is characterized by what is stated in the characterizing part of claim 1.

Further, the active agents of the invention for medical use according to the invention is characterized by what is stated in claim 22, and the method of the present invention is characterized by what is stated in claim 23.

Considerable advantages are obtained by means of the invention. Thus, the present invention provides a composition and method for preventing or at least decreasing the incidence or number of headache episodes in subjects suffering from severe headaches, such as cluster headaches or migraine.

The compositions are effective for releasing the active agents in a food product or drink (including water or any beverages), particularly in cases where these food products or drinks contain alcohol, acetaldehyde, yeast or sugars. Preferably, in these cases, the composition is added to the food product or the drink in connection with the consumption, i.e. eating or drinking. In practice, the composition is added to the food product or drink just before eating or drinking.

The compositions are also effective for releasing the active agents in the mouth or in the stomach, and binding acetaldehyde, in particular, when they are consumed in connection with eating or drinking, i.e. just before, during or just after eating or drinking, or in connection with smoking. In practice, the compositions are generally administered while the subject sits at the dining table, or immediately before lighting a cigarette (or beginning the use of another tobacco product) or immediately after putting the cigarette out.

However, despite the here implied local effect, the compositions also have a systemic effect, due to the additional active agent, selected from cystine, glutathione and methionine. This additional active agent is transformed into cysteine in the body, but said transformation mainly takes place after the agent has passed the stomach, whereby it will be transferred via the small intestine into the blood stream, to provide a wider area of action (via the systemic route), and a broader range for the effect.

The compositions can be used also in a continuous manner, for example after every 8 to 10 hours. The composition comprises one or more carriers that regulate the release of the active agents, thus giving a continuous effect.

Next, the invention will be described more closely with reference to the attached drawings and a detailed description.

DETAILED DESCRIPTION OF THE PREFERRED EMBODIMENTS OF THE INVENTION

The present invention concerns a non-toxic solid pharmaceutical composition for oral administration, containing one or more cysteine compound from the group of L-cysteine, D-cysteine and N-acetyl cysteine as active agents, combined with one or more additional active agents, at least one of which being selected from cystine, glutathione and methionine, the composition being intended for reducing the incidence of, or even preventing severe headaches.

The term "cysteine compound" is intended to mean a cysteine, such as L- or D-cysteine, or a derivative or salt thereof, particularly N-acetyl cysteine. The function of this main active agent is based on the local effect obtainable through the reaction of this cysteine compound in the gastrointestinal tract.

The function of the mentioned additional active agent(s) selected from cystine, glutathione and methionine is based on the capability of these agents to be transformed into cysteine or to provide a similar effect as cysteine, although systemically.

The partially local and partially systemic effects are possible due to the different reactivities of these groups of active agents in the gastrointestinal tract. The main cysteine compound will react, particularly with the acetaldehyde, in the stomach, while the additional active agent selected from cystine, glutathione and methionine will be transferred, mainly via the small intestine, to the blood stream before reacting.

According to an embodiment of the invention, the composition further contains diamine oxidase (i.e. histaminase) as an active agent for degrading excess histamine.

According to a preferred embodiment, the active agents, however, consist of amino acids selected from L-cysteine, D-cysteine, N-acetyl cysteine, cystine, glutathione and methionine.

According to another embodiment, a vitamin or a similar nutritious supplement is further included in the composition. This supplementary agent can be, for example, a taurine compound or a common water-soluble vitamin, such as vitamin C, $B_2$ or $B_5$, due to the contents of reactive functional groups of these compounds, or a salt thereof. Preferably, the supplementary agent is vitamin C or a salt of taurine, such as a magnesium or calcium salt, due to the additional neuro-muscular activity of such salts. More preferably the supplementary agent is a magnesium taurinate, most suitably magnesium N-acetyl taurinate. These compounds have here been found to further reduce the incidence of, or even prevent severe headaches.

The composition may be formulated into, for example, a tablet, a capsule, a granule, or a powder, or optionally into a tablet or a capsule filled with said powder or granules. Thus, the composition may be formulated into a monolithic or multiparticular preparation. The composition for release in a foodstuff or a drink (including water and any beverages) is preferably formulated into and added to said foodstuff or drink in the form of a powder or granules. The composition for administration into and release in the mouth or the stomach of the subject, in turn, is preferably administered as a capsule, tablet or lozenge, most suitably as a capsule enclosing the active agents and additives in granulated form.

The function of the cysteine or the N-acetyl-cysteine is based on the neutralization of the acetaldehyde formed during smoking or during the consumption of alcohol, or of alcohol- or acetaldehyde-containing foodstuff or drinks, including foodstuff and drinks that contain materials that are capable of forming alcohol or acetaldehyde prior to or just after consumption, such as certain bacteria, yeasts or carbohydrates.

The above mentioned optional vitamins and supplements function by amplifying the acetaldehyde-binding effect of the cysteine compound.

The function of the cystine, the glutathione or the methionine is, in turn, based on its low reactivity in the gastrointestinal tract, whereby it is conducted directly to the small intestine in its original form, where it will firstly be transformed into cysteine and react with any remains of acetaldehyde carried past the stomach, and secondly be carried to the blood stream and further on to the organs, particularly the liver, to eliminate any acetaldehyde formed in these organs.

The function of the diamine oxidase (i.e. histaminase) is based on its enzymatic activity in degrading histamine, whereby this further cause of severe headaches is reduced.

Definitions

The composition of the present invention comprises an effective amount of one or more agent from the group of L-cysteine, D-cysteine and N-acetyl cysteine, as well as of one or more agent selected from cystine, glutathione and methionine. The glutathione can be present in the composition in either oxidized or reduced form. Preferably, the reduced form is used, since this will provide an increased local effect, while the oxidized form can be targeted to the systemic route of action. Optionally, also an effective amount of diamine oxidase, a taurine compound or a common water-soluble vitamin can be included in the composition.

An "effective amount" means an amount capable of binding or inactivating an amount of acetaldehyde present in a foodstuff, alcohol, other drink or tobacco, or formed during the consumption of foodstuff, alcohol or other drink, or after eating or drinking, or formed during or after smoking, or at least keeping the acetaldehyde content essentially lower than without the use of the composition. In case of diamine oxidase, an effective amount means an amount capable of degrading an excess of histamine temporarily formed in the subject.

Keeping the acetaldehyde content essentially lower than without the use of the composition means that the acetaldehyde content should be kept at a level that is at least 20%, preferably over 40%, and most preferably over 60% lower than when not using the composition according to the description of the invention.

The mentioned acetaldehyde is mainly formed in the saliva of the subject. Due to the deposition of acetaldehyde into the aerodigestive tract, the acetaldehyde also reaches the esophagus and stomach via normal wash-out of saliva. Further, the alcohol reaching further into the blood-stream will be spread throughout the body and into the organs, where it can cause harm as such, or can be transformed into acetaldehyde. Thus, the harm is, at least to a small extent, systemic. However, a mere systemic effect or a mere local effect does not remove the problem.

Such a harmful content of acetaldehyde mainly in the human mouth, oesophagus, stomach or small intestine or large intestine, and to a small extent in the other areas of the body, can be formed in connection with consuming alcoholic drinks, particularly strong alcoholic drinks, or foodstuffs containing alcohol, or as a consequence of smoking, or when consuming products containing acetaldehyde, in particular in people having atrophic gastritis or an achlorhydric stomach.

"Alcoholic drinks" are ethanol-containing drinks, their ethanol content varying within 0.7% by volume and 84% by volume."

"Alcoholic foodstuffs" refer to foodstuffs containing at least 0.7% of ethanol. Such foodstuffs can be, for example, fermented juices or preserves, or foodstuffs preserved with small amounts of alcohol, pastries, jellies, and mousse seasoned with liqueur or corresponding products containing alcohol.

"Acetaldehyde comprising foodstuffs" refers to foodstuffs containing acetaldehyde. Acetaldehyde is contained in foodstuffs, wherein ethanol has been generated in connection with fermentation, such as beer, cider, wine, home-brewed beer, and other alcoholic drinks, as well as many juices. In certain foodstuffs, such as some milk products, acetaldehyde is used for preservation purposes and to add flavour, or the acetaldehyde is formed in the product as a consequence of microbial activity. For example, sugary juices or sugar-containing foodstuffs in general, provide a food substrate for such microbes. High concentrations of acetaldehyde are formed, for example, in fermented milk products, such as yoghurt. The microbes used to make yoghurt produce acetaldehyde in the yoghurt. As for alcoholic drinks, sherry and Calvados contain especially large amounts of acetaldehyde.

The use of the compositions according to the invention can be of benefit even in connection with consuming light alcoholic drinks or foodstuffs, these drinks or foodstuff containing only small amounts of alcohol.

"In connection with consuming alcoholic drinks" herein refers to the period of time that begins when the subject starts to consume alcoholic drinks and ends when there is no more alcohol in the blood of the subject. However, this term, as such, is not intended to restrict the invention to a reaction of the alcohol in the blood.

Since the compositions of the invention can be beneficial also "in connection with consuming drinks", where the drinks contain materials capable of forming alcohol or acetaldehyde in the body of the subject, or containing only small amounts of alcohol (thus not forming a measurable alcohol content in the blood), the time period can optionally be interpreted to begin 10 to 0 minutes before the subject drinking and ending about 10 minutes after drinking.

Similarly, "in connection with eating" herein refers to the period of time starting 10 minutes before the subject eating and ending 10 minutes after eating.

The composition can, for example, be mixed with the foodstuff or it can be administered before or after eating.

"Smoking", as such, would refer to the use of a tobacco product by inhalation, such as the smoking of a cigarette, cigar or pipe. However, tobacco can be used, for example, by smoking, chewing, wetting or snuffing, and a "tobacco product" refers to any tobacco product, such as a cigarette, cigar, pipe, snuff or chewing tobacco. Thus, "in connection with smoking" herein refers to any use of a tobacco product during a period of time that begins from starting to use tobacco and ends, when said use is stopped.

However, according to our research, smoking, in particular, seems to cause the formation of acetaldehyde in the mouth.

COMPOSITIONS OF THE INVENTION

The composition of the present invention contains, as active agents, one or more agents from the group of L-cysteine, D-cysteine and N-acetyl cysteine, as a combination with one or more agents selected from cystine, glutathione and methionine, in any of the forms previously described, the composition optionally including further active agents.

According to an embodiment of the invention, the composition further contains diamine oxidase (i.e. histaminase) as an active agent for degrading excess histamine.

According to another embodiment, a taurine compound or a common water-soluble vitamin is included in the composition.

The composition further comprises one or more pharmaceutical additives, preferably including one or more non-toxic carriers that provide controlled release of said compounds in the desired area(s) of the body.

Controlled release here means the local release of the cysteine compound during at least 5 minutes in the conditions of the mouth, preferably 5 to 15 minutes, or at least 30 minutes in the conditions of the stomach, preferably 0.5 to 8 hours, while the cystine or the glutathione or the methionine is conducted directly to the small intestine for release into the blood stream.

According to the invention, the products obtained from the binding of acetaldehyde to the active agents are safe and non-toxic for the organism.

In addition to cysteines and their derivatives, as well as the cystine, the glutathione and the methionine, the scope of the invention also includes the salts of these compounds, specifically pharmaceutically acceptable salts, in particular water-soluble salts.

It is of advantage to further add to the compositions of the present invention at least one of the substances selected from the group comprising chromium, vitamin B12, A-, D-, E, -C-vitamins, niacin, biotin, thiamine, B2-, B5-, B6-vitamins and folic acid and trace elements, such as chromium, manganese, selenium, zinc and iron, and anti-microbials that decrease acetaldehyde formation, as these further improve the desired effect. As stated above, the vitamins C, B2 and B5 are particularly useful, especially vitamin C.

Another useful compound to be added to the composition of the invention, which can amplify the acetaldehyde-binding effect of the composition, is also lecithin.

However, only those compounds (and in those amounts), which are non-toxic and suitable for human consumption, are applied to the compositions according to the present invention.

A unit dose of the composition according to the invention can be in the form of, for example, a powder, a tablet, a capsule, a lozenge or a chewing gum. The possibly used tablet can be in a form of a monolithic or multiparticular preparation, while the possibly used capsule can contain the active agents and the additives in, e.g. powder or granule form. Most suitably, the compositions of the invention are formulated into capsules containing the active agents as well as one or more suitable additives, most suitably in granulated form.

The granules, tablets and capsules can be covered by a water-soluble film, which effectively covers or masks the taste of the active agents.

The compositions intended for release in foodstuff or drinks, prior to consumption, can be formulated into for example, powders, which are easily mixed into the foodstuff or drink.

In the case of such a powder, the content of the active agents in the composition can vary between 0.2 to 2 w-% of cysteine and 0.2 to 2 w-% of cystine or glutathione or a combination thereof. The additives typically include agents that mask the taste of the active agents, such as sweeteners or flavourings.

The compositions intended for release in the mouth can be formulated into for example tablets or other preparations, which can be placed between the cheek or the lip and the gum, or preparations that are sucked or chewed in the mouth.

According to the simplest alternative, the unit doses for release in the mouth can be prepared by simply mixing the solid substances, optionally moistured by ethanol, and formulating them into a suitable form, e.g. by pressing into tablets.

The compositions intended for release in the stomach can be formulated into for example tablets or capsules to be swallowed.

In case of a chewing gum, the content of the active agents in the composition can vary between 0.2 to 2 w-% of cysteine and 0.2 to 2 w-% of cystine, glutathione or methionine, or a combination thereof.

In this case, the composition also includes a gum base, in a content of 90 to 99 w-% of the composition, preferably in an amount of 500 to 1500 mg per unit dose.

In case of a lozenge or a tablet to be kept in the mouth, the content of active agents in the composition can vary between 0.3 to 20 w-% of cysteine and 0.3 to 20 w-% of cystine, glutathione or methionine, or a combination thereof.

In this case, the composition also includes one or more diluting agent or filler, in a content of 85 to 98 w-% of the composition, preferably in an amount of 50 to 750 mg per unit dose.

In case of a tablet or capsule to be swallowed, the content of active agents in the composition can vary between 0.5 to 20 w-% of cysteine and 0.5 to 20 w-% of cystine, glutathione or methionine, or a combination thereof.

In these cases, the composition also includes one or more bulking agents, in a content of 85 to 98 w-% of the composition, preferably in an amount of 50 to 750 mg per unit dose.

All types of formulations preferably include an amount of cysteine that is 2 to 50 mg per unit dose, and an amount of cystine, glutathione or methionine, or a combination thereof, that is 2 to 50 mg per unit dose.

According to a preferred embodiment, the composition contains a total amount of active agents, particularly of cysteine compound and additional active agent, which is 2 to 100 mg per unit dose, preferably 2 to 50 mg per unit dose, more preferably 4 to 20 mg per unit dose, and most suitably 5 to 10 mg per unit dose.

Only small amounts/doses are required due to the local area of action of the cysteine, whereby the cysteine is not diluted in any significant extent, and due to the synergistic effect of the active agents, with both the cysteine and the cystine or the glutathione or the methionine relieving the headaches of the subject and thus providing a reduced incidence of headaches via several routes simultaneously. This provides a surprisingly strong effect.

The release of the active compounds in the conditions of the mouth usually takes place in amounts of 15 to 25 mg per hour. In the stomach, the rate of release is generally 40 to 80 mg per hour.

1 or 2 preparations according to the invention can be administered at a time and the administration can be repeated at 2 to 10-hour intervals, most preferably at 4 to 8-hour intervals. In case of chewing gums, a longer interval of 6 to 10 hours can be used, since one gum, after chewing, can be tucked in between the cheek and gums, and chewed again later to release more active agents.

The composition can be formulated to release its active agents in a controlled manner in the mouth or in the stomach.

According to one preferred embodiment of the invention the composition is to release the active agents in the mouth, and comprises, for the purpose of controlling the release, a carrier, usually in the form of a polymer, that does not dissolve or dissolves only poorly in the mouth (hereafter called "a carrier/polymer that does not dissolve in the mouth").

The polymer not dissolving in the mouth can be any pharmaceutically acceptable additive, such as metacrylate polymer, for example Eudragit RS or S, or ethyl cellulose (EC).

The carrier can also be selected from those forming a gel that adheres to the mucous membranes in the mouth. Such carriers are generally selected from pharmaceutically acceptable polymers. More specifically, the carrier can be selected from the group comprising various chitosans, alginates, such as sodium alginate, aluminium hydroxide, sodium hydrogen carbonate, sodium carboxymethyl cellulose, and sodium hydrogen carbonate.

In addition to the active agents and optional carrier(s), the composition can comprise, for example:

1. Pharmaceutically acceptable diluents (fillers, extenders),
2. Sweeteners, such as sugars and sugar alcohols,
3. Flavourings, and
4. Slip additives/lubricants.

The sugars can comprise, for example, saccharose, fructose or glucose or mixtures thereof. The sugar alcohols can comprise mannitol, sorbitol, maltitol, lactitol, isomalt, or xylitol or mixtures thereof. Preferably, none of the used additives react with the other ingredients in the composition. Not being too sweet, a preferable sweetener comprises mannitol, and its amount in the composition can be quite large; accordingly, it simultaneously functions as a diluent.

The flavourings can comprise, for example, spearmint, peppermint, menthol, citrus fruit, *eucalyptus* or aniseed or a mixture thereof.

The composition can also comprise other ingredients, such as substances that prevent bad oral smell, substances that function as breath fresheners and/or prevent dental caries, or the preparation can comprise vitamins. The composition can also comprise substances that increase salivation.

Further, the composition can comprise, as a further additive, a bulking agent, preferably an inert agent, particularly in a content of 20-70 w-%, preferably 40 to 60 w-%, most preferably about 50 w-%.

The inert bulking agent can be for example dicalcium hydrogen phosphate, microcrystalline cellulose (MCC), or another corresponding non-swelling agent.

According to a preferred embodiment of the present invention, a typical preparation/unit dose (such as one tablet) for release in the mouth can comprise or consist of the following:

| | |
|---|---|
| Cysteine | 2 to 10 mg |
| Cystine/glutathione/methionine | 2 to 10 mg |
| Diluting agent(s)/sweetener(s) | 50 to 750 mg |
| Flavouring(s) | q.s. |
| Lubricant(s) (0.5 to 3% by weight) | 5 to 25 mg |

The tablets can be prepared by mixing a powdery mass and compressing it into sucking tablets by any well-known methods.

If the amount of cysteine or cystine or glutathione or methionine is increased, the amount of diluent(s)/sweetener(s) and flavourings can also be increased, as the taste of the cysteine preferably is disguised.

A typical preparation/unit dose can be formulated into a chewing gum, and essentially comprises or consists of the following:

| | |
|---|---|
| Cysteine | 2 to 10 mg |
| Cystine/glutathione/methionine | 2 to 10 mg |
| Gum base (comprising e.g. sweeteners) | 500 to 1500 mg |
| Flavouring | q.s. |
| Lubricant (0.5 to 3% by weight) | 5 to 30 mg |

The gum base can be formed from medicated chewing gum (Morjaria, Y. et al., Drug Delivery Systems & Sciences, vol. 4, No. 1, 2004) or natural or synthetic elastomers, softeners, waxes or lipids. Natural gum bases, including crude rubber and smoked natural rubber, are permitted by the FDA. However, modern gum bases are mostly synthetic and include styrene-butadiene rubber, polyethylene and polyvinyl acetate.

The gum base generally constitutes 15 to 40 w-% of a chewing gum. The remaining portion includes mainly medicating agents, sugars, sweeteners, softeners, flavourings and colouring agents.

The majority of the chewing gum-based drug delivery systems are prepared using conventional methods. However, directly compressible powder gums are modern alternatives to the medicated chewing gums. Pharmagum is a compressible new gum system. It is a mixture of polyol(s) and/or sugars with a gum base. A formulation that contains Pharmagum gums can be compressed into a gum tablet by using conventional tablet presses. The manufacturing method is quick and inexpensive. The amount of gum base in the preparation, comprising sweeteners, can be 50 to 500 mg, preferably 500 to 1500 mg.

Pharmagum S contains rubber base and sorbitol, Pharmagum M contains rubber base, mannitol, and isomalt.

The composition can be prepared by mixing a powdered mass and compressing it into chewable pieces.

The preparation can be a buccal tablet comprising:

| | |
|---|---|
| Cysteine | 2 to 10 mg |
| Cystine/glutathione/methionine | 2 to 10 mg |
| Non-ionized macro molecules | 5 to 25 mg |
| Ionizing macro molecules | 2 to 10 mg |
| Flavouring(s) | q.s. |
| Lubricants | 0.5 to 3% by weight |

The non-ionized macro molecules include, e.g., methylcellulose (MC), hydroxypropyl cellulose (HPC) and hydroxypropyl methylcellulose (HPMC), and polyethylene glycol (PEG). The ionizing polymers include, e.g., sodium carboxymethyl cellulose (NaCMC), alginic acid, sodium alginate, chitosan, polycarbofile (Noveon™) and carbomer (Capropol™).

The non-ionized macro molecules generally constitute 40 to 80 w-% of a buccal tablet, whereas the ionizing polymers generally constitute 20 to 60 w-% of such a tablet.

The preparation can also be a sublingual tablet essentially comprising or consisting of the following:

| | |
|---|---|
| Cysteine | 2 to 10 mg |
| Cystine/glutathione/methionine | 2 to 10 mg |
| Diluent(s)/sweetener(s) q.s. | 50 to 500 mg |
| Flavouring(s) | q.s. |
| Lubricants | 0.5 to 3% by weight |

The diluents include, e.g., lactose, calcium phosphates, starch, carboxymethyl cellulose, hydroxymethyl cellulose. The sweetener can be, for example, mannitol or xylitol.

The diluents generally constitute 90 to 98 w-% of a sublingual tablet.

According to another preferred embodiment of the invention, the composition is formulated to release the active agents in the stomach, and comprises, for the purpose of controlling the release, a carrier, such as a polymer, that does not dissolve or dissolves only poorly in the stomach (here called simply "a carrier/polymer that does not dissolve in the stomach"). The composition is, for this purpose, preferably formulated by pressing it into tablets or by enclosing the composition into capsules. Alternatively the composition can be covered by a water insoluble film.

A carrier not dissolving in the stomach can be a polymer, such as metacrylate polymer, for example Eudragit RS or S, or ethyl cellulose.

Such polymers are preferably present in a content of 10-50 w-%, more preferably 20 to 40 w-%, most suitably 20 to 30 w-% of the entire composition.

The carrier can also form a gel in the stomach that floats in the contents of the stomach, or the composition can be formulated into a liquid preparation taken orally (mixture), the physical structure of which preferably is a gel. Alternatively, the carrier of the composition can attach to the mucous membrane of the stomach, thus causing the entire preparation, including active agent, to attach to the mucous membrane.

The composition can also comprise a bulking agent, preferably an inert agent, such as dicalcium hydrogen phosphate, microcrystalline cellulose (MCC), or another corresponding non-swelling agent, for example in a content of 20-70 w-%, preferably 40 to 60 w-%, most preferably about 50 w-%, of the entire composition.

According to one preferred embodiment of the invention the composition comprises matrix granules not dissolving in stomach. Such a composition can comprise for example:

| | |
|---|---|
| Cysteine | 5 to 40 w-% (preferably 25 w-%) |
| Cystine/glutathione/methionine | 5 to 40 w-% (preferably 25 w-%) |
| Polymer not dissolving in stomach | 10 to 50 w-% (preferably 20 to 30 w-%) |
| Inert bulking agent | 20 to 70 w-% (preferably 40 to 60 w-%) |
| Ethanol | q.s. |

The polymer not dissolving in stomach can in the above composition be any commonly used additive, such as metacrylate polymer, for example Eudragit RS or S, or ethyl cellulose (EC). The inert bulking agent may be for example dicalcium hydrogen phosphate, microcrystalline cellulose (MCC), or other corresponding non-swelling agent. The solid substances are mixed and moistured by ethanol. The moisture mixture is granulated by using in pharmaceutical industry well known methods and devices. The dried granules can be used as such or distributed into dosages, for example into capsules.

According to another preferred embodiment of the invention the composition comprises matrix tablets not dissolving in stomach. Such a composition can comprise for example:

| | |
|---|---|
| Cysteine | 5 to 40 w-% (preferably 25 w-%) |
| Cystine/glutathione/methionine | 5 to 40 w-% (preferably 25 w-%) |
| Polymer not dissolving in stomach | 10 to 50 w-% (preferably 20 to 30 w-%) |
| Inert bulking agent | 20 to 70 w-% (preferably 20 to 50 w-%) |

The polymer not dissolving in stomach may in the above composition be any in pharmaceutical industry commonly used additive, such as metacrylate polymer, for example Eudragit RS or S, or ethyl cellulose (EC). The inert bulking agent can be, for example, dicalcium hydrogen phosphate, microcrystalline cellulose (MCC), or another corresponding non-swelling agent. The solid substances are mixed and the mixture is granulated by using, for example, ethanol or a hydrophilic polymer solution. The granules are pressed into tablets using methods and devices well known in the pharmaceutical industry. The release of the active compound(s) is here based on the diffusion of the water-soluble effective compound(s) from the pores formed to the tablet matrix.

According to another preferred embodiment of the invention the composition comprises one or more porous film forming agents for coating the preparation, such as ethyl cellulose or hydroxypropyl methylcellulose, or a combination thereof. Most suitably a combination of ethyl cellulose and hydroxypropyl methylcellulose is used, such as a combination with a relative amount of EC to HPMC being 3/2 to 7/3.

Such a composition covered by a porous film can comprise, for example:

| | |
|---|---|
| Cysteine | 1 to 50 w-% (preferably 20 to 50 w-%) |
| Cystine/glutathione/methionine | 1 to 50 w-% (preferably 20 to 50 w-%) |
| Water-soluble bulking agent(s) | 50 to 80 w-% (preferably 30 to 60 w-%) |
| Porous film forming agent(s) | q.s. |

The water-soluble bulking agent can, in such a composition, be for example lactose or some other water-soluble bulking agent commonly used in the pharmaceutical industry. The solid substances are mixed and the mixture is pressed into tablets using methods and devices well-known in the pharmaceutical industry. The porous film can be prepared from a water-soluble polymer, such as hydroxypropyl methyl cellulose (HPMC), or a water-insoluble polymer, such as ethyl cellulose (EC), preferably from a mixture of such polymers. The relative amount of the film forming substances, for example EC and HPMC, is preferably 2-5 parts water-insoluble polymer and 1-2 parts water-soluble polymer. In the conditions of the stomach the water-soluble polymer dissolves and pores are formed in the remaining water insoluble polymer. The release of the effective compound(s) is here based on the diffusion of the water-soluble effective compound(s) from the pores formed in the film. The film forming substances effectively mask also the taste of the active agent(s).

Treatment

The composition comprising effective amounts of cysteine and cystine or glutathione or methionine is administered into the foodstuff or drink soon to be consumed by a subject, or directly to the subject, in a suitable amount, which can contain, for example, 0.2 to 20 w-% of cysteine and 0.02 to 20 w-% of cystine or glutathione or methionine or a combination thereof, most suitably directly to the subject in connection with the subject consuming alcohol-containing drinks or foodstuff, or acetaldehyde-containing drinks or foodstuff, or in connection with the subject smoking.

Furthermore, it is preferred that the preparation has a shape that makes it easy to keep in the mouth or to swallow. However, it is of advantage if the composition for release of active agents in the stomach is in the form of a preparation having a diameter of at least 7 mm, preferably 8 to 15 mm, more preferably 11 to 15 mm. This assists the preparation to stay in the stomach sufficient time for the controlled release of the active agents.

Thus, the present invention provides preparations and methods, which can be used to reduce the incidence of severe headaches, particularly cluster headaches and migraines.

For example, the incidence of severe headaches can be reduced using a method of treatment that comprises the following stages:
 a) a human subject at least occasionally suffering from severe headaches is provided with a composition containing cysteine and cystine or glutathione or methionine, to be administered in connection with consuming alcoholic drinks or foodstuff, or acetaldehyde-containing drinks or foodstuff, or in connection with smoking,
 b) the subject self-administers the composition, and
 c) the subject is allowed to eat, drink or smoke,
whereby the cysteine and the cystine or the glutathione or the methionine bind the acetaldehyde generated or carried to the body in connection with consuming the drink or the foodstuff, and
 d) optionally, the stages a) to c) are repeated as many times as feels necessary.

OTHER APPLICATIONS OF THE INVENTION

According to an embodiment of the invention the composition of the present invention is administered to human subjects having atrophic gastritis, in addition to suffering from said severe headaches.

Atrophic gastritis, among others, enhances the risk of malabsorption of vitamin B12, and may lead to pernicious anemia. Malabsorption of micronutrients may lead to serious secondary diseases of the central nervous system and to osteoporosis. Half of the people with atrophic gastritis of corpus of the stomach can have an exceptionally low vitamin B12 level and at least half of these simultaneously have increased serum levels of homocysteine. Thus, the composition of the present invention, supplemented with vitamin B12, is particularly suitable for use by such people. The vitamin B12 will be released with the other active agents and carried with at least a portion of the cystine or the glutathione or the combination thereof to the blood stream for a systemic effect.

Vitamin B12 deficiency is a strong risk factor for neurodegenerative disorders, such as dementia, depression and polyneuropathies. The deficiency of vitamin B12 is one common reason for hyperhomocysteinemia, an independent risk factor for atherosclerosis, strokes and heart attacks. Because of corpus atrophy and poor diet even 15% of individuals over the age 50 are suffering from a preventable epidemic of vitamin B12 deficiency.

With the early detection of corpus atrophy by routine screening for suitable biomarkers, for example by GastroPanel® screening, and subsequent treatment, possible neurological disabilities (e.g. dementia, depression and polyneuropathies) and vascular diseases (e.g. stokes and heart attacks) can be prevented. The ageing of the population is increasing the need for screening for said biomarkers, for example by the GastroPanel® examination and screening, and, in other words, for diagnosis of atrophic gastritis and related risks and diseases.

To the compositions of the present invention, in addition to vitamin B12, also other vitamins can be added, such as vitamins A, D, E and C, niacin, biotin, thiamine, B2, B5, B6 and folic acid as well as trace elements, such as chromium, manganese, selenium, zink and iron. Ferrous compounds are of particular advantage, since atrophic gastritis is often connected with iron deficiency anemia.

According to an embodiment of the invention, the above-described treatment is preceded by a diagnosis as to a possible H. pylori infection, preferably using a test that reliably provides a diagnosis also as to atrophic gastritis. Thus, the magnitude of the problems caused by acetaldehyde in the gastrointestinal tract (GI tract) can be estimated.

It is clear from the literature that the biomarkers pepsinogens I and II (PG-I and PG-II) as well as gastrin-17 (G-17) measure atrophic gastritis accurately, possibly on the average even more accurately than gastroscopy. The PG I/PG II ratio also correlates with the occurrence of precancerous and cancerous changes in the oesophagus. These biomarkers are secreted into the stomach lumen, and small quantities are transferred to the circulation where they reflect the concentrations in the stomach.

The level of PGI and the ratio PGI/PGII are markers of the function and structure of the corpus mucosa, and the level of G-17, which is usually measured in a fasting blood sample, is a marker of the function and structure of the antrum mucosa. Including for example H. pylori antibodies, such as H. pylori IgG and IgA, as biomarkers in the test will provide information also as to a possible H. pylori infection. Thus, said biomarkers (PG-I, PG-II and their ratio in combination with G-17 and H. pylori IgG and IgA) complement each other so as to form a diagnostic panel.

The levels of these biomarkers are preferably measured using an ELISA assay on a blood, plasma or serum sample of a patient, particularly on a fasting plasma sample. If a patient with an H. pylori infection and low levels of G-17 does not want to have invasive gastroscopy, atrophic gastritis of the antrum can be confirmed or excluded by assaying the concentration of protein-stimulated G-17 in plasma in addition to said examination from a fasting plasma sample. An examination procedure particularly suitable for said purpose is the GastroPanel® examination.

The role of PG-I as a marker of atrophic gastritis is well known. Lately also evidence regarding its usefulness in determining the condition of particularly the corpus mucosa has been provided.

The PGI/PGII ratio has lately been shown to decrease linearly with increasing grade of atrophic gastritis in the corpus. The ratio is <3.0 when atrophic gastritis is advanced (moderate or severe) in the gastric corpus. It has been shown that the risk of gastric cancer is increased (5-fold) when the PGI/PGII ratio is low.

The role of measuring the amidated peptide hormone gastrin-17 is less studied than the pepsinogens, but yet already of considerable clinical interest. In the stomach, gastrin-17 has the task of stimulating the secretion of hydrochloric acid. Likewise, there is a negative feed-back control such that hydrochloric acid inhibits the formation of G-17.

Combining the G-17 determination with those of PG I and II helps to distinguish the cases where the atrophic gastritis (AG) is limited to the gastric fundus and corpus regions (PG-I is low, but G-17 is high), from those where also the antrum is affected (both PG-I and G-17 are low). Such a distinction is clinically important, because the latter (panatrophy) carries the highest known risk for gastric cancer.

To sharpen the examination further, a fasting G-17 assay may be compared with a determination after stimulation by a protein meal. If a low G-17 level is not clearly raised by such stimulation, it provides good evidence for atrophy in the antrum domain. However, if an initially low G-17 level is clearly raised by such stimulation, the gastric antrum is likely to be physiologically functional, and a low resting G-17 level (e.g., below 2 pmol/L) is in such cases a strong indication of abnormally high acidity in the stomach, in which case the risk of Barrett's oesophagus is elevated. Conversely, a pathologically high level of fasting G-17 is strongly indicative of hypo- or achlorhydria, which may be caused by AG limited to the corpus region, or indeed by PPI treatment.

The following examples are included merely for illustrative purposes, and are not intended to limit the invention.

EXAMPLES

Example 1—Preparation of Sucking Tablets

Sucking tablets were prepared, one type comprising:

| | |
|---|---|
| L-Cysteine | 20 mg |
| Cystine | 20 mg |
| Mannitol (or an equivalent sugar or sugar alcohol) | 750 mg |
| Flavouring | q.s. |
| Magnesium stearate | 10 mg |

The further compositions varied in cysteine content, which was 1.25 mg, 2.5 mg, 5 mg, and 10 mg of cysteine.

The compositions were prepared by mixing a powdery mass and compressing it into sucking tablets.

Example 2—Preparation of Chewing Gums

A chewing gum was prepared, comprising:

| | |
|---|---|
| Cysteine | 20 mg |
| Cystine | 20 mg |
| Pharmagum S, M or C | 1000 mg |
| Flavouring | q.s. |
| Magnesium stearate | 20 mg |

The composition was prepared by mixing a powdery mass and compressing it into chewing gums.

Another composition was prepared, comprising 500 mg of Pharmagum S or M, and 20 mg of magnesium stearate.

Example 3—Preparation of Buccal Tablets

A buccal tablet was prepared, comprising:

| | |
|---|---|
| Cysteine | 20 mg |
| Cystine | 20 mg |
| Methocel | 25 mg |
| Carbopol | 7 mg |
| Flavouring | q.s. |
| Magnesium stearate | 2 mg |

The composition was prepared by mixing a powdery mass and compressing it into buccal tablets.

Example 4—Preparation of Sublingual Tablets

A sublingual tablet was prepared, comprising:

| | |
|---|---|
| Cysteine | 10 mg |
| Cystine | 10 mg |
| Mannitol | 250 mg |
| Flavouring | q.s. |
| Magnesium stearate | 5 mg |

The composition was prepared by mixing a powdery mass and compressing it into sublingual tablets.

Example 5—Effect of the Composition on Acetaldehyde Levels

Five smokers (of the age of 29±2.8) participated in a study, in which three cigarettes were smoked (with cleaning periods in between). While smoking each cigarette (in 5 minutes time), the voluntaries sucked tablets blindfold, containing a placebo, 1.25 mg, 2.5 mg, 5 mg, 10 mg or 20 mg of L-cysteine. The acetaldehyde in the saliva samples was analysed by gas chromatography after 0, 5, 10, 20 minutes from starting to smoke.

Figure 1:
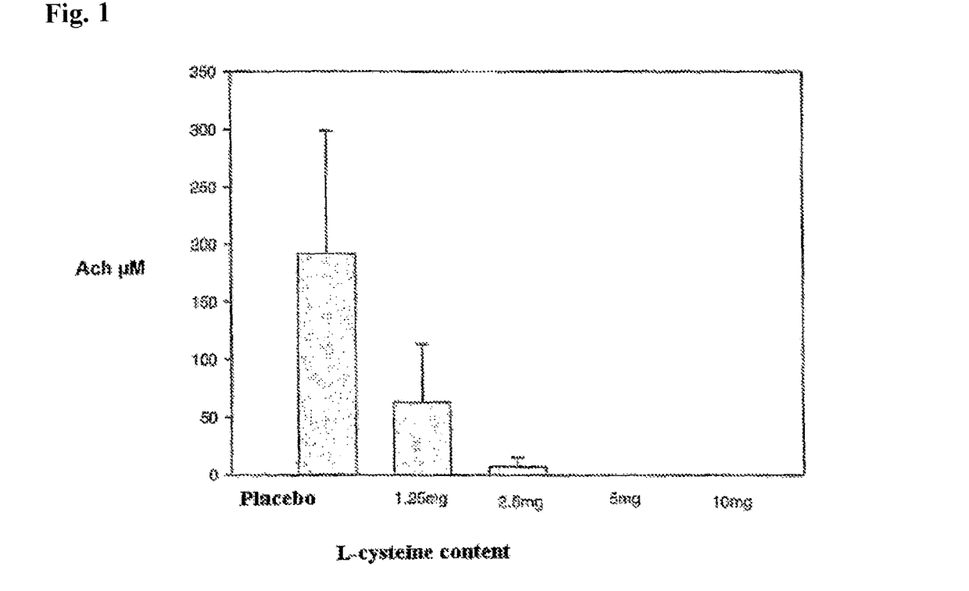
FIG. 1 demonstrates the effect of compositions containing cysteine in different amounts on the acetaldehyde levels of the saliva.

The L-cysteine tablets (5 mg, 10 and 20 mg) removed from the saliva all of the acetaldehyde originating from tobacco (see FIG. 1). The average salivary acetaldehyde contents immediately after smoking were 191.2±48.5 µM, 0 µM, 0 µM, 0 µM with the placebo and the 5 mg, 10 mg, and 20 mg L-cysteine tablets, respectively.

The study showed that even 5 mg of L-cysteine, when delivered with a melting tablet, completely inactivated the carcinogenic acetaldehyde in the saliva during smoking. The L-cysteine tablet of 1.25 mg reduced the amount of acetaldehyde by about two thirds compared with the placebo.

Figure 2:
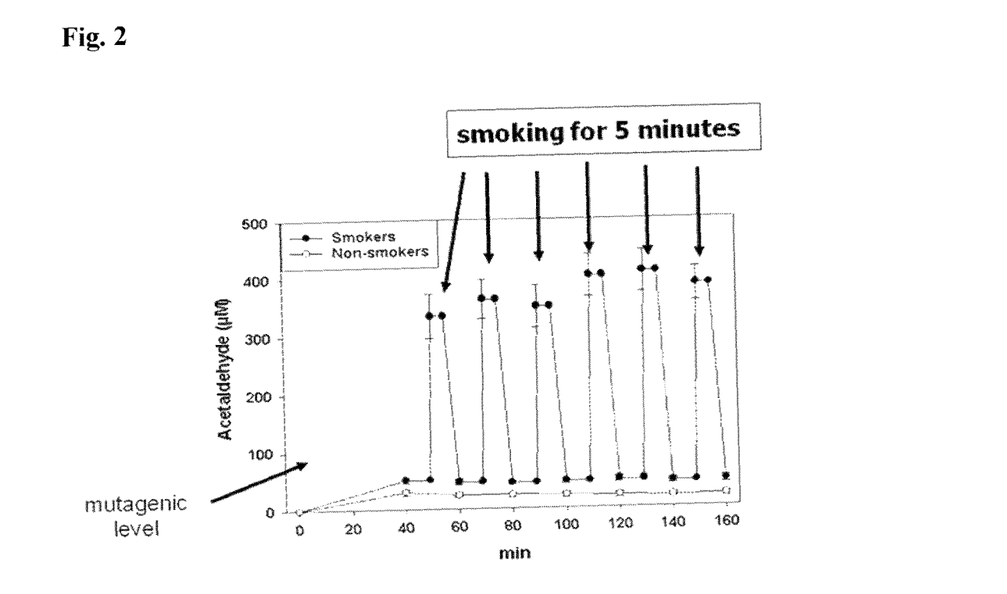
FIG. 2 demonstrates the changes in the salivary acetaldehyde levels during smoking.

Example 6—Increase in Salivary Acetaldehyde Levels Following Smoking and Drinking Tobacco smoke contains acetaldehyde, which during smoking becomes dissolved in saliva (see FIG. 2). In this study, both smokers and non-smokers at first took a small dose of alcohol and thereafter the smokers smoked 6 cigarettes for about 5 minutes each. During smoking, salivary acetaldehyde exceeds remarkably the carcinogenic level.

Via swallowing, the salivary acetaldehyde derived either from alcohol or smoking is distributed from the oral cavity to the pharynx, the oesophagus and the stomach. Thus, the carcinogenic effect is not limited to the mouth.

The strongest evidence for the local carcinogenic action of acetaldehyde provides studies with ALDH2-deficient Asians, who form an exceptional human "knock-out model" for long-term acetaldehyde exposure.

In the subjects with ALDH2-deficiency (Flushers) the additional salivary acetaldehyde appeared to be derived from salivary glands.

In several epidemiological studies from Asian countries it has been uniformly shown that ALDH2-deficiency associates with over 10-fold risk of upper digestive tract cancers. The association is strongest among heavy drinkers but in addition significant also among normal alcohol consumers. Thus, smokers are clearly also at high risk.

In conclusion, acetaldehyde derived from tobacco appears to act in the upper digestive tract as a local carcinogen in a dose-dependent and synergistic way.

Example 7—Acetaldehyde-Elimination Using Cysteine

Cysteine is a sulfur-containing amino acid. Its average intake is about 1 g/day. Cysteine condensates with and thereby deactivates the reactive and carcinogenic acetaldehyde by forming 2-methyl-thiazolidine-4-carboxylic acid (MTCA).

Figure 3:
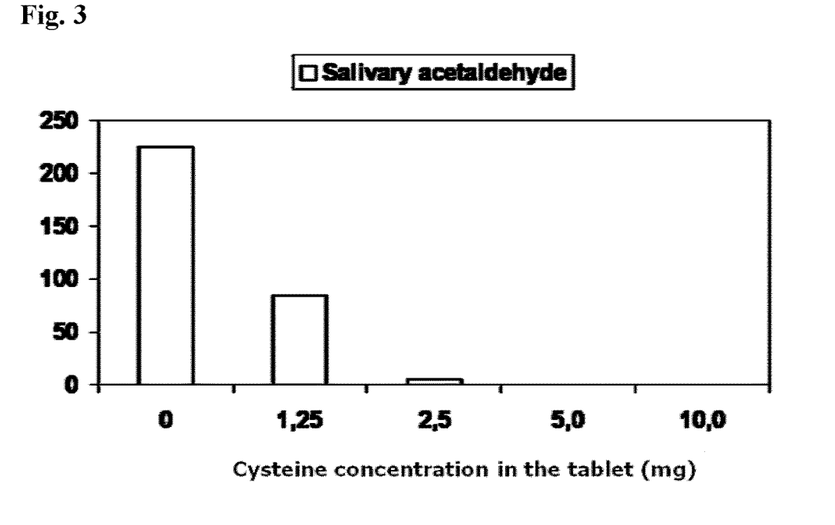
FIG. 3 demonstrates the binding of the acetaldehyde formed during smoking using cysteine.

For example a lozenge containing as little as 5 mg of L- or D-cysteine totally eliminates acetaldehyde from saliva during smoking (FIG. 3).

Figure 4:
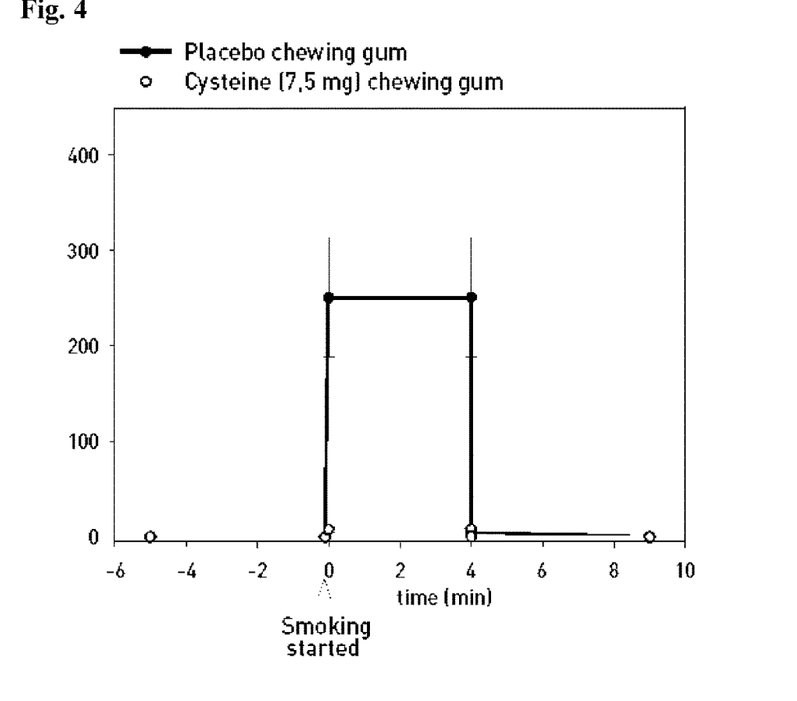
FIG. 4 demonstrates the effect of a chewing gum containing L-cysteine (7.5 mg) on salivary acetaldehyde levels during smoking, as compared to the use of a placebo chewing gum.

Harmful effects of reactive acetaldehyde may be prevented by binding it to the cysteine. This semi-essential amino acid inactivates acetaldehyde by a non-enzymatic binding, forming a more stable compound, 2-methylthiazolidine-4-carboxylic acid. For example, a tablet and chewing gum containing L-cysteine has been developed in order to eliminate acetaldehyde exposure during smoking (FIG. 4).

The invention claimed is:

1. A non-toxic solid pharmaceutical composition for oral administration, for reducing the incidence of migraine or cluster headaches, the composition containing one or more cysteine compound from the group of L-cysteine, D-cysteine and N-acetyl cysteine as active agents, characterized in that the cysteine compound is combined with one or more additional active agents, at least one of which being selected from the group of cystine, glutathione and methionine, the composition further containing one or more pharmaceutical additives, including one or more non-toxic carriers that provide controlled release of the active agents either into the saliva during at least 5 minutes in the conditions of the mouth or into the stomach during at least 15 minutes in the conditions of the stomach.

2. The composition of claim 1, characterized in that it is in the form of a powder, tablet, lozenge, capsule or chewing gum.

3. The composition of claim 1, characterized in that the active agents are selected from L-cysteine and one or more of cystine, glutathione and methionine.

4. The composition of claim 1, characterized in that the active agents are selected from one or more cysteine compounds and glutathione.

5. The composition of claim 1, characterized in that it further contains diamine oxidase as an active agent for degrading excess histamine.

6. The composition of claim 1, characterized in that the active agents consist of amino acids selected from L-cysteine, D-cysteine, N-acetyl cysteine, cystine, glutathione and methionine.

7. The composition of claim 1, characterized in that it further contains a vitamin or a similar nutritious supplement selected from a taurine compound or a common water-soluble vitamin, such as vitamin C, $B_2$ or $B_5$, or a salt thereof.

8. The composition of claim 1, characterized in that it contains a total amount of active agents, particularly of cysteine compound and additional active agent, which is 2 to 50 mg per unit dose, preferably 2 to 20 mg per unit dose, and most suitably 4 to 10 mg per unit dose.

9. The composition of claim 1, characterized in that it is formulated for controlled release of the active agents in the mouth or the stomach, or for release into a food product or drink prior to consumption.

10. The composition of claim 9, characterized in that the amount of cysteine compound in a formulation for release of the active agents in the mouth is 2 to 10 mg per unit dose, whereas the amount of cystine or glutathione or methionine or a combination thereof in such a formulation is 2 to 10 mg per unit dose, and the amount of cysteine in a formulation for release of the active agents in the stomach is 10 to 50 mg per unit dose, whereas the amount of cystine or glutathione or methionine or a combination thereof in such a formulation is 10 to 50 mg per unit dose.

11. The composition of claim 1, characterized in that it comprises, as additives, diluents, such as fillers or extenders, sweeteners, such as sugars or sugar alcohols, flavorings, lubricants, gum base, non-ionized polymers or ionizing polymers, or a combination of two or more of these.

12. The composition of claim 11, characterized in that the gum base is selected from natural or synthetic elastomers, softeners, waxes and lipids.

13. The composition of claim 11, characterized in that the non-ionized polymers are selected from methylcellulose (MC), hydroxypropyl cellulose (HPC) and hydroxypropyl methylcellulose (HPMC), and polyethylene glycol (PEG).

14. The composition of claim 11, characterized in that the ionizing polymers are selected from sodium carboxymethyl cellulose (NaCMC), alginic acid, sodium alginate, chitosan, polycarbofile and carbomer.

15. The composition of claim 11, characterized in that the diluents are selected from lactose, calcium phosphates, starch, carboxymethyl cellulose, hydroxymethyl cellulose.

16. The composition of claim 1, characterized in that it has been formulated into chewing gums, wherein the gum base constitutes 15 to 40% of a chewing gum, the remaining portion including agents selected from medicating agents, sugars, sweeteners, softeners, flavorings and coloring agents.

17. The composition of claim 1, characterized in that it has been formulated into buccal tablets containing non-ionized macro molecules in a content of 40 to 80 w-% and ionizing polymers in a content of 20 to 60 w-%.

18. The composition of claim 1, characterized in that it has been formulated into sublingual tablets containing diluents in a content of 90 to 98 w-%.

19. The composition of claim 1, characterized in that it has been formulated into matrix granules or matrix tablets containing polymers not dissolving in the stomach in a content of 10 to 50 w-%, and bulking agent in a content of 20 to 70 w-%.

20. The composition of claim 1, characterized in that it is dosed by placing 1 or 2 preparations formulated from the composition in the mouth at a time and replacing them with new ones at 4 to 10-hour intervals.

21. A combination of one or more cysteine compounds, selected from L-cysteine, D-cysteine and N-acetyl cysteine, with one or more of the compounds cystine, glutathione and methionine for use as a medicine.

22. A method for reducing the incidence of severe headaches in human subjects, characterized by carrying out the following stages:
 a) providing a subject that at least occasionally suffers from severe headaches with a composition according to claim 1, to be self-administered in connection with consuming alcoholic drinks or foodstuff, or acetaldehyde-containing drinks or foodstuff, or in connection with smoking,
b) allowing the subject to self-administer said composition, and
c) allowing the subject to eat, drink or smoke,
whereby the cysteine and the cystine or the glutathione or the methionine bind the acetaldehyde generated in or carried to the body in connection with the subject consuming the drink or the foodstuff, and
d) optionally, repeating the stages a) to c) as many times as feels necessary.

23. The method of claim 22 for reducing the incidence of migraine or cluster headaches.

24. The method of claim 22, characterized by administering the composition to the subject in step b) by placing 1 or 2 preparations formulated from the composition in the mouth or swallowing them, and the optional step d) is carried out by replacing the preparations with new ones at 4 to 10-hour intervals, most preferably at 6 to 8-hour intervals, and optionally also repeating step c).

25. The composition of claim 3, characterized in that in that the active agents are selected from L-cysteine and one of cystine, glutathione and methionine.

26. The composition of claim 25, characterized in that the active ingredients are L-cysteine and glutathione.

27. The composition of claim 4, characterized in that the active agents are selected from one cysteine compound and glutathione.

28. The composition of claim 7, characterized in that it further contains a vitamin or a similar nutritious supplement selected from vitamin C or a salt of taurine, which is selected from a magnesium or calcium salt.

29. The composition of claim 28, characterized in that it further contains a vitamin or a similar nutritious supplement selected from magnesium taurinates.

30. The composition of claim 29, characterized in that the supplement is magnesium N-acetyl taurinate.

31. The composition of claim 10, characterized in that the amount of cysteine compound in a formulation for release of the active agents in the mouth is about 5 mg, whereas the amount of cystine or glutathione or methionine or a combination thereof in such a formulation is about 5 mg, and the amount of cysteine in a formulation for release of the active agents in the stomach is about 20 mg, whereas the amount of cystine or glutathione or methionine or a combination thereof in such a formulation is about 20 mg.

32. The composition of claim 12, characterized in that the gum base is selected from crude rubber and smoked natural rubber, and the synthetic gum base is selected from styrene-butadiene rubber, polyethylene and polyvinyl acetate.

33. The composition of claim 20, characterized in that the preparations are replaced in the mouth at 6 to 8-hour intervals.

* * * * *